United States Patent [19]
Genet et al.

[11] Patent Number: 5,614,641
[45] Date of Patent: Mar. 25, 1997

[54] PROCESS FOR ENANTIOSELECTIVE HYDROGENATION OF THE OXO C=O DOUBLE BOND

[75] Inventors: Jean-Pierre Genet, Verrières-Le-Buisson; Sylvain Juge, "Le-Champ-des-Cordes"; Jean-Alex Laffitte, Pau; Catherine Pinel, Ablis; Serge Mallart, Orsay, all of France

[73] Assignee: Elf Aquitaine, France

[21] Appl. No.: 362,557

[22] PCT Filed: Jun. 30, 1993

[86] PCT No.: PCT/FR93/00663

§ 371 Date: Mar. 5, 1995

§ 102(e) Date: Mar. 9, 1995

[87] PCT Pub. No.: WO94/01390

PCT Pub. Date: Jan. 20, 1994

[30] Foreign Application Priority Data

Jul. 2, 1992 [FR] France .................... 92 08160

[51] Int. Cl.⁶ .................. C07D 307/32; C07C 35/08; C07C 27/00; C07C 64/76
[52] U.S. Cl. .................. 549/313; 560/55; 560/56; 560/126; 560/129; 568/799; 568/832; 568/861
[58] Field of Search ........................ 560/55, 56, 126, 560/129; 568/799, 832, 861; 549/313, 263; 556/14, 19, 21, 136; 502/152, 155

[56] References Cited

U.S. PATENT DOCUMENTS

| | | | |
|---|---|---|---|
| 4,343,741 | 8/1982 | Townsend et al. | 548/412 |
| 5,159,093 | 10/1992 | Taketomi et al. | 556/136 |
| 5,274,146 | 12/1993 | Ishizaki et al. | 556/14 |
| 5,286,888 | 2/1994 | Sano et al. | 556/21 |
| 5,306,834 | 4/1994 | Takaya et al. | 549/263 |
| 5,324,861 | 6/1994 | Ishizaki et al. | 568/454 |
| 5,430,191 | 7/1995 | Foricher et al. | 568/12 |
| 5,481,008 | 1/1996 | Broger et al. | 549/292 |

FOREIGN PATENT DOCUMENTS

| | | |
|---|---|---|
| 0158875 | 10/1985 | European Pat. Off. |
| 0295109 | 12/1988 | European Pat. Off. |
| 0295890 | 12/1988 | European Pat. Off. |
| 0339764 | 11/1989 | European Pat. Off. |
| 0484271 | 5/1992 | European Pat. Off. |
| 9212110 | 7/1992 | WIPO |

Primary Examiner—C. Warren Ivy
Assistant Examiner—Raymond Covington
Attorney, Agent, or Firm—Ostrolenk, Faber, Gerb & Soffen, LLP

[57] ABSTRACT

The present invention concerns a process for enantioselective catalytic hydrogenation of the ketone C=O double bond to a secondary alcohol function, said process using a neutral ruthenium complex as the catalyst and a compound containing a C=O group as the substrate to be hydrogenated, characterised in that it comprises hydrogenation of the substrate using a diallyl (diphosphino) ruthenium compound with formula

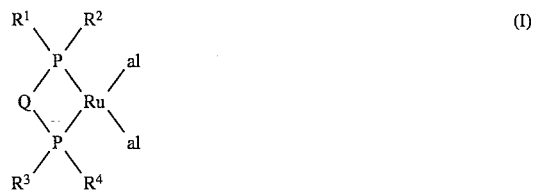

(I)

where
al preferably represents $CH_2CH=CH_2$ or $CH_2C(CH_3)=CH_2$,
Q represents a hydrocarbon bridge containing at least two catenary carbon atoms and which can contain one to four catenary heteroatoms selected from O, S, N and Si,
$R^1$ to $R^4$ may be identical or different and each represents a $C_1$–$C_{18}$ alkyl, $C_5$–$C_7$ cycloalkyl or $C_6$–$C_{12}$ aryl group.

15 Claims, No Drawings

PROCESS FOR ENANTIOSELECTIVE HYDROGENATION OF THE OXO C=O DOUBLE BOND

FIELD OF THE INVENTION

The present invention concerns a novel enantioselective catalytic hydrogenation process for the oxo C=O, or ketone, double bond. This novel process produces an enantiomerically pure or highly pure secondary alcohol from a ketone. It uses a neutral ruthenium complex.

PRIOR ART

Hydrogenation of the C=O carbonyl function to produce a primary alcohol which does not contain an asymmetrical carbon atom when the carbonyl function is constituted by a formyl group and to produce a secondary alcohol function containing an asymmetrical carbon atom when the carbonyl function is constituted by an oxo (i.e. ketone) group is known to occur via the following mechanisms:

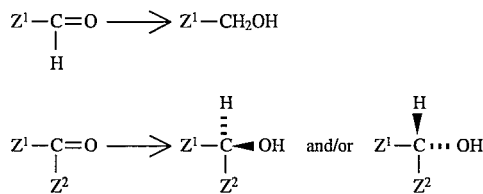

Hydrogenation of a ketone C=O double bond generally produces a compound containing a secondary alcohol function which is constituted by a mixture of enantiomers. That mixture is then treated to isolate the enantiomer which is deemed to be important using a known method which is generally long and tedious. These treatments include chiral chromatography (especially HPLC) and fractionated crystallisation.

In order to overcome the problems associated with this type of isolation, ruthenium complexes, especially those containing acetate or halide groups, have been proposed for use as enantioselective hydrogenation catalysts for the ketone C=O carbonyl function; see, for example, POWEL et al., J. Chem. Soc., (1968), pp 159–161, R. NOYORI et al., J. Am. Chem. Soc., (1987), pp 5856–5858, M. KITAMURA et al., J. Am. Chem. Soc., (1988), 110, pp 629–631, and T IKARIYA et al., J. Chem. Soc., Chem. Comm., (1985), p 922.

The use of ruthenium based catalysts from the group of complexes known as "ionic", on the one hand, and "neutral", on the other hand, is known in the field of hydrogenation of ethylenically unsaturated organic compounds containing at least one aliphatic C=C double bond.

French patent application No 90 165 414 filed 28 Dec. 1992 (publication number FR-A-2 671 079, published 3 Jul. 1992) and the corresponding International application PCT/FR 91/01077 filed 27 Dec. 1991 describe catalysts for the catalytic hydrogenation of ethylenically unsaturated compounds, the catalysts being "neutral" ruthenium complexes in which: (i) two tertiary phosphine groups are bonded to the same Ru atom, the P atoms of said tertiary phosphine groups being bonded together by a chain containing at least two catenary atoms, and (ii) two allyl or methallyl residues are bonded to the same Ru atom.

The Ru complexes described in the above French patent application and international application are diallyl (diphosphino) ruthenium compounds which can be represented by the following formula I:

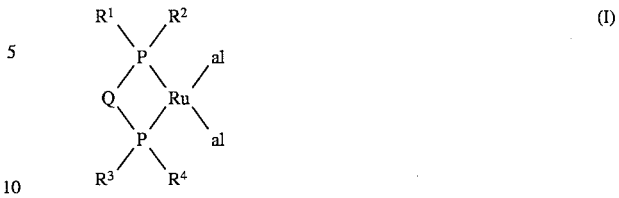

where
al represents an allyl group,
Q represents a hydrocarbon bridge containing at least two catenary carbon atoms and which can contain one to four catenary heteroatoms selected from O, S, N and Si,
$R^1$ to $R^4$ may be identical or different and each represents a $C_1$–$C_{18}$ alkyl, $C_5$–$C_7$ cycloalkyl or $C_6$–$C_{12}$ aryl group.

The allyl groups al defined above include all allyl groups. The simplest and most economical are the allyl group itself with formula $CH_2CH=CH_2$ and in particular the methallyl group with formula $CH_2C(CH_3)=CH_2$, hereinafter abbreviated to "Met".

OBJECTS OF THE INVENTION

One object of the invention is to provide a novel catalytic hydrogenation process for the ketone C=O double bond without substantially affecting the carbonyl C=O group included in any carboxylic acid group —C(=O)—OH, carboxylate group —C(=O)—O— or carboxamide group —C(=O)—NH— which may be present in the ketone which is to be reduced to an alcohol.

A further object of the invention is to provide a novel catalytic hydrogenation process for the ketone C=O double bond which can produce optically active secondary alcohols in a yield greater than 85%, preferably greater than 90% and most preferably in the order of 99% to 100% with respect to the starting ketones, along with e.e of at least 35%.

In accordance with the invention, optically active secondary alcohols are prepared for use as intermediate compounds for the production of enantiomerically pure products which are used in other fields, in particular for therapeutic purposes.

SUMMARY OF THE INVENTION

The objects defined above and other advantages are accomplished by means of the present invention. More precisely, in its broadest aspect, the invention provides a novel use of the Ru complexes with formula I defined above for catalytic hydrogenation of the ketone C=O double bond. Said complexes have until now been recommended only for catalytic hydrogenation of the C=C double bond in ethylenically unsaturated compounds as described in international patent application PCT/FR 91/01077 cited above (this document being hereby incorporated herein by way of reference).

The invention thus provides a novel process for enantioselective catalytic hydrogenation of the ketone C=O double bond to a secondary alcohol function, said process using a neutral ruthenium complex as the catalyst and a compound containing a C=O function as the substrate to be hydrogenated, characterised in that the process comprises hydrogenation of the carbonyl ketone function of the substrate in an appropriate solvent using $H_2$ (preferably at a pressure of $10^5$ Pa to $1.5 \times 10^7$ Pa, at a temperature of −20° C. to 150° C., and in the presence of 0.01 molar % to 10 molar % with respect to said substrate), using a diallyl (diphosphino) ruthenium compound with formula

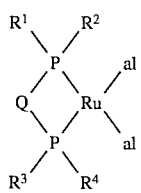

(I)

where al represents an allyl group, preferably $CH_2CH=CH_2$ or $CH_2C(CH_3)=CH_2$, Q represents a hydrocarbon bridge containing at least two catenary carbon atoms and which can contain one to four catenary heteroatoms selected from O, S, N and Si, $R^1$ to $R^4$ may be identical or different and each represents a hydrocarbon group which may be substituted, selected from $C_1$–$C_{18}$ alkyl, $C_5$–$C_7$ cycloalkyl and $C_6$–$C_{12}$ aryl groups.

This process is of particular interest for the hydrogenation of substrates such as (i) diketones and (ii) compounds containing at least one ketone function and at least one other function, e.g. alpha- and betaketoesters.

This process can also be used for the production of compounds containing particular secondary alcohol functions which are optically active and usable as intermediate compounds for the stereospecific synthesis of other products, e.g. those which are important for human and veterinary therapeutic purposes.

ABBREVIATIONS

The following abbreviations will be used in the present description, for convenience:

al=allyl or methallyl;
BDPP=2,4-bis(diphenylphosphino) pentane

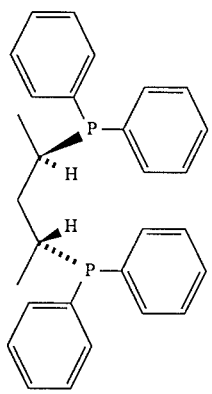

BINAP=2,2'-bis(diphenylphosphino)-1,1'binaphthyl

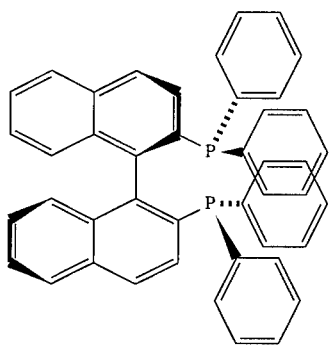

Boc=t-butyloxycarbonyl;
bNp=betanaphthyl (i.e. 2-naphthyl);
BNPE=bis(naphthylphenytphosphino) ethane

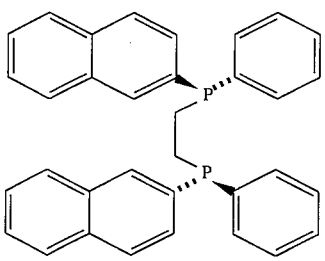

BNPPMDS=bis(2-naphthylphenylphosphinomethano) diphenylsilane

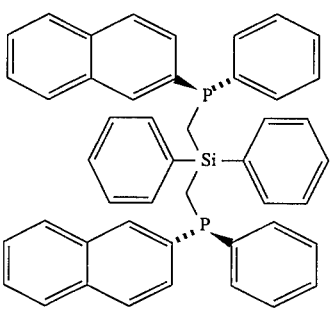

BPPM=N-Boc-4-diphenylphosphino-2-(dimethylphosphinomethyl)-pyrrolidine

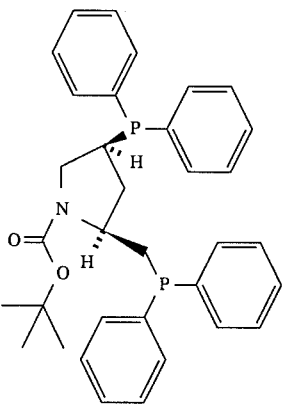

Bu=n-butyl
Bz=benzyl
CHIRAPHOS=2,3-bis(diphenylphosphino) butane

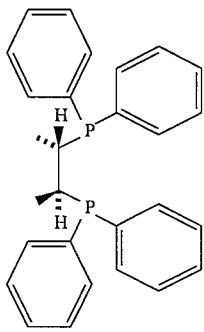

DIOP=O,O-isopropylidene-2,3-dihydroxy-1,4-bis (diphenylphosphino) butane

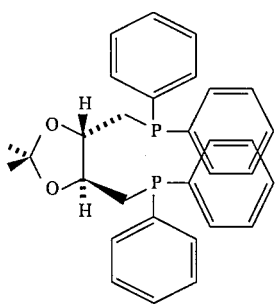

DIPAMP=1,2-bis (phenyl o-anisylphosphino) ethane

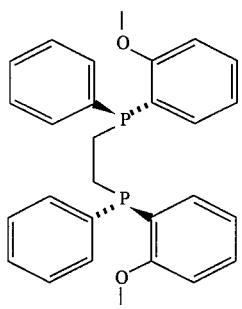

also called (R,R)-1,2-bis (phenyl ortho-anisylphosphino) ethane;
Et=ethyl;
HPLC=high performance liquid chromatography;
i-Pr=isopropyl;
Me=methyl;
MeO=methoxy;
Met=methallyl [i.e. CH$_2$C(CH$_3$)=CH$_2$];
Ph=phenyl;
Pr=n-propyl;
RT=room temperature (15° C.–20° C.);
s-Bu=sec-butyl;
t-Bu=tert-butyl;
THF=tetrahydrofuran.

DETAILED DESCRIPTION OF THE INVENTION

As indicated above, groups $R^1$, $R^2$, $R^3$ and $R^4$, which may be identical or different, each represent a hydrocarbon group which may be substituted, selected from $C_1$–$C_{18}$ alkyl, $C_5$–$C_7$ cycloalkyl and $C_6$–$C_{12}$ aryl groups. Advantageously, groups $R^1$, $R^2$, $R^3$ and $R^4$, which may be identical or different, each represent a $C_1$–$C_8$ alkyl group (e.g. methyl, ethyl, isopropyl, propyl, s-butyl, i-butyl, t-butyl, 2,2-dimethylpropyl or 1,1,3,3-tetramethylbutyl), a $C_5$–$C_7$ cycloalkyl group (e.g. cyclopentyl or preferably cyclohexyl) or a $C_6$–$C_{12}$ aryl group (e.g. phenyl, tolyl, xylyl, halogenophenyl, p-methoxyphenyl, p-ethoxyphenyl, p-(t-butyloxy)phenyl or naphthyl).

Preferably, $R^1$, $R^2$, $R^3$ and $R^4$, which may be identical or different, each represent a cyclohexyl group, a phenyl group, a phenyl group which is substituted in the para position by a $C_1$–$C_4$ alkyl group, a phenyl group which is substituted in the para position by a $C_1$–$C_4$ alkoxy group, or a phenyl group which is substituted in the para position by a F, Cl, Br or 2-naphthyl group.

The hydrocarbon chain of bridge Q is either an unsaturated chain, or a saturated chain. For example, bridge Q may have one of the following structures:

(a) —(CH$_2$)$_n$—, or
(b) —(CH$_2$)$_m$—A—(CH$_2$)$_p$— where n, m and p, which may be identical or different, each represent a whole number from 1 to 6, A represents O, S, PR, SiR$_2$ or NR, where R is a $C_1$–$C_4$ alkyl group, a $C_5$–$C_6$ cycloalkyl group, a $C_6$–$C_{10}$ aryl group, a benzyl group or a phenethyl group.

When bridge Q contains 2 to 4 catenary atoms, it can have one of the following structures:

 (S1)

 (S2)

(S3)

 (S4)

(S5)

(S6)

 (S7)

 (S8)

 (S9)

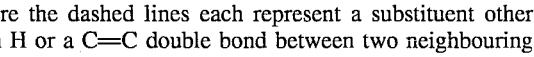 (S10)

where the dashed lines each represent a substituent other than H or a C=C double bond between two neighbouring carbon atoms which may be part of a cycle; thus structure (S9) above of bridge Q could be:

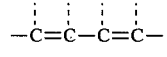

With regard to these definitions, bridge Q could be selected from the group constituted by, for example:

(a1) —CH$_2$—,
(a2) —CH$_2$CH$_2$—,
(b1) —CH$_2$—O—CH$_2$—,
(b2) —CH$_2$—S—CH$_2$—,
(b3) —CH$_2$—P(Ph)—CH$_2$—,
(b4) —CH$_2$—Si(Me)$_2$—CH$_2$—,
(b5) —CH$_2$—Si(Ph)$_2$—CH$_2$—,
(b6) —CH$_2$—Si(Bz)$_2$—CH$_2$—,
(b7) —CH$_2$—Si(Et)$_2$—CH$_2$—, or
(b8) —CH$_2$CH$_2$—P(Ph)—CH$_2$CH$_2$.

Advantageously, the catalyst of the invention has formula $$L^*Ru\,(Z)_2 \quad (II)$$

where

Z is Met, and

L* is a chiral diphosphino type ligand where the two phosphorus atoms are bonded together by a hydrocarbon bridge containing at least two catenary carbon atoms which can contain one to four catenary heteroatoms selected from O, S, N and Si.

In formula (II), chiral ligand L* represents the divalent system R$^1$R$^2$P-Q-PR$^3$R$^4$ (from formula I), advantageously where R$^1$ to R$^4$ are each an aryl group (preferably Ph or bNp), which may be substituted, or a cyclohexyl group, and Q is a hydrocarbon bridge with a catenary chain which can be partially or completely included in the cycle.

Examples of suitable chiral ligands L* are BDPP, BINAP, BNPE, BNPPMDS, BPPM, CHIRAPHOS, DIOP and DIPAMP as defined above in the section headed "ABBREVIATIONS", also analogous ligands, especially those described in the literature, e.g. BPPM, CyDIOP, CyPRONOP, Cy-cy CAPP, CyPOP AE, DEGUPHOS, DPCB, NORPHOS, PNNP, PROPHOS and SKEWPHOS, the majority of which are described in international patent application PCT/FR 91/01077 cited above.

Preferred "neutral" ruthenium complexes with formula II for enantioselective catalytic hydrogenation of compounds containing a ketone C=O double bond are those in which the chiral ligand L* is DIOP or BINAP.

Chiral compounds with formulae I and II which are diallyl (diphosphino) ruthenium compounds can be prepared using a known method.

The recommended method for their preparation is described in international patent application PCT/FR 91/01077 cited above.

The hydrogenation process of the invention comprises treating a substrate, in this case a compound containing a carbonyl ketone function, with H$_2$ in an appropriate inert solvent in the presence of a diallyl (diphosphino) ruthenium compound with formula I, or preferably with formula II, as the catalytic hydrogenation catalyst, under the following preferred conditions:

a temperature of between −20° C. and +150° C.;
a pressure of between 10$^5$ Pa and 1.5×10$^7$ Pa, and
a catalyst/substrate molar ratio of between 0.01/100 and 10/100.

A particularly preferred value of the temperature of the hydrogenation reaction is greater than or equal to 15° C. In practice, the catalytic hydrogenation of the invention is carried out at a temperature of 15° C. to 100° C. at a pressure of H$_2$ in the order of 5×10$^5$ Pa to 10$^7$ Pa.

Even more advantageously, the process for catalytic hydrogenation of the ketone C=O double bond of the invention is carried out under the following conditions:
a temperature of between 25° C. and 50° C.;
a pressure of H$_2$ between 5×10$^6$ Pa and 10$^7$ Pa, and
a catalyst/substrate molar ratio of between 0.5/100 and 4/100.

The hydrogenation period is not critical. It is usually one hour or more. Depending on the substrate and the catalyst, it can be between 10 hours and 70 hours, for example.

Particular examples of suitable solvents are alcohols such as anhydrous MeOH, EtOH and PrOH, aromatic hydrocarbons such as benzene, toluene and xylene, aliphatic hydrocarbons such as pentane, hexane, heptane and the like, halogenated hydrocarbons such as CH$_2$Cl$_2$, ClCH$_2$—CH$_2$Cl and Cl$_2$CH—CHCl$_2$, ethers, e.g. cyclic ethers such as THF, and mixtures thereof. Preferred solvents are toluene and CH$_2$Cl$_2$.

When the hydrogenation reaction of the invention is carried out, it is recommended that the substrate is used at a concentration of 0.2 mole/liter to 1.5 mole/liter, preferably 0.4 mole/liter to 0.8 mole/liter in the solvent.

In addition, a small quantity of a tertiary amine can be added to the reaction medium, e.g. Et$_3$N, to improve the yield in very particular cases, especially when the solvent for the reaction medium is MeOH. This addition is not essential, however, and can even be a constraint when producing methyl (R)-2-chloromandelate from methyl (2-chlorophenyl)-oxoacetate, as will be shown below. Nevertheless, when such an addition is effected, the tertiary amine is introduced into the reaction medium in a quantity corresponding to (i) a tertiary amine/solvent weight ratio in the order of 1/100 or (ii) a tertiary amine/substrate molar ratio analogous to or identical to the catalyst/substrate molar ratio.

DESCRIPTION OF THE PREFERRED EMBODIMENT

The preferred embodiment of the process of the invention, particularly for producing methyl (R)-2-chloromandelate from methyl (2-chlorophenyl) oxoacetate, consists in hydrogenating the ketone substrate to be reduced in a solvent selected from CH$_2$Cl$_2$ and toluene in the presence of a catalyst with formula II where L* is DIOP or BINAP, under the following conditions:
a temperature of between 25° C. and 50° C.;
a pressure of H$_2$ between 5×10$^6$ Pa and 10$^7$ Pa,
a catalyst/substrate molar ratio in the order of 1/100, and
a substrate concentration of between 0.4 mole/liter and 0.8 mole/liter.

Other advantages and features of the invention will become apparent from the following hydrogenation examples and comparative tests. These examples are, of course, non-limiting and are given by way of illustrative example only. In particular, the person skilled in the art can determine the following by means of simple tests, without departing from the scope of the invention: (i) the chiral catalyst with formula I or preferably formula II (e.g. the choice of ligand L*), (ii) the solvent and (iii) the operating conditions most suitable for hydrogenation of a given ketone substrate.

OPERATING CONDITIONS

Reduction of the Ketone C=O Double Bond Using a Ruthenium Complex 5.9×10$^{-4}$ mole of alpha-ketoester in 2 ml of solvent was added to a test tube containing 6×10$^{-6}$ mole of a catalyst with formula I of the invention using a PIPETMAN GIBSON apparatus. The test tube was then placed under argon in a reactor and purged three times with H$_2$. The reaction medium was vigorously stirred using a magnetic stirrer (for at least one hour, the stirring time varying between 10 hours and 64 hours depending on the example), at a set temperature and pressure. At the end of the reaction, the solvent was evaporated off under vacuum (glass filter pump). A dark viscous liquid was obtained. This method A was used in the following examples, with modifications regarding the nature of the substrate and/or the quantities of catalyst and substrate as necessary.

EXAMPLE 1

Production of (R)-pantolactone

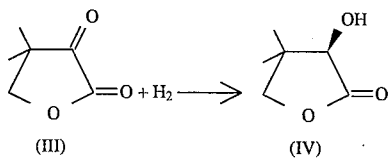

(R)-pantotactone with formula IV, which has the name L-dihydro-3-hydroxy-4H-dimethyl-2(3H)-furanone or L-3-hydroxy-4,4-dimethyl-tetrahydrofuran-2-one in the systematic nomenclature, is an enantiomer used in the synthesis of the enantiomer L-(+)-pantothenic acid, which is the only isomer of pantothenic acid which acts as a vitamin.

Catalytic hydrogenation of the compound with formula III (carbonyl substrate), which has the systematic nomenclature name 4,4-dimethyl-tetrahydrofuran-2,3-dione, was carried out in the presence of DIPAMP Ru (Met)$_2$ and Et$_3$N under the following conditions:
temperature: 50° C.;
pressure of H$_2$: $1.013 \times 10^7$ Pa (100 arm);
molar ratio: DIPAMP Ru (Met)$_2$/substrate: 1/100;
time: 64 h;
solvent: toluene;
substrate concentration: 0.5 mole/l;
molar ratio: Et$_3$N/substrate: 1/100.

The enantiomer with formula IV was obtained in a yield of 100% (calculated from the starting substrate) and an enantiomeric excess (e.e) of 14%.

EXAMPLES 2–4 AND COMPARATIVE EXAMPLE CP1

Production of ethyl (R)-4-chloro-3-hydroxybutanoate, precursor of carnitine (vitamin BT, an important pharmacological agent, responsible for human metabolism and transport of fatty acids across mitochondrial boundaries).

$$Cl-CH_2-C(=O)-CH_2-C(=O)-OEt + \quad (V)$$

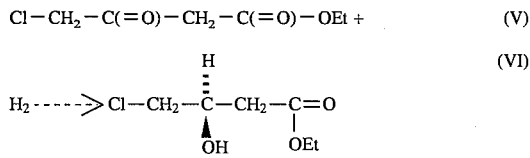

Catalytic hydrogenation of substrate V to produce enantiomer VI was carried out under the following conditions:
catalyst: BINAP Ru (Met)$_2$, BINAP Ru (Br)$_2$ or CHIRAPHOS Ru (Met)$_2$;
temperature: 80° C. or 90° C.;
pressure of H$_2$: $10^7$ Pa;
catalyst/substrate molar ratio: 0.1/100 or 1/100;
time: 10 h;
solvent: MeOH;
substrate concentration: 0.5 mole/ml.

The operating conditions used are shown in Table I below, along with the yield and e.e.

These results show that catalyst BINAP Ru (Met)$_2$ gave a greater yield and e.e than BINAP Ru (Br)$_2$ and that catalyst CHIRAPHOS Ru (Met)$_2$ was not very enantioselective in this instance.

EXAMPLES 5–6 AND COMPARATIVE EXAMPLES CP 2–CP 3

Production of methyl (R)-2-chloromandelate

The following reaction was carried out:

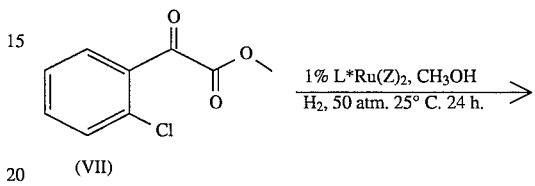

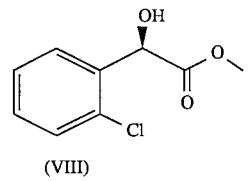

to produce methyl (R)-2-chloromandelate from methyl (2-chlorophenyl) oxoacetate with formula VII under the following conditions:
catalyst: see Table II;
temperature: 25° C.;
pressure of H$_2$: $5.065 \times 10^6$ Pa (50 atm);
catalyst/substrate molar ratio: 1/100;
time: 24 h;
solvent: MeOH;
substrate concentration: 0.5 mole/ml.

The yield and e.e obtained are shown in Table II below.

EXAMPLES 7–8 AND COMPARATIVE EXAMPLE CP 4

Production of methyl (R)-2-chloromandelate

The enantiomer with formula VIII was obtained as described above for Examples 5–6, replacing the methanol solvent with toluene, The results obtained are shown in Table III below.

EXAMPLES 9–10

Production of methyl(R)-2-chloromandelate

The enantiomer with formula VIII was obtained as described above for Examples 5–6, replacing the methanol with another solvent (either MeOH+1% Et$_3$N or THF).

The results obtained are shown in Table IV below.

EXAMPLES 11–13 AND COMPARATIVE EXAMPLE CP 5

Production of methyl(R)-2-chloromandelate

The enantiomer with formula VIII was obtained as described above for Examples 5–6, replacing the methanol solvent with dichloromethane.

The results obtained are shown in Table V below.

EXAMPLES 14–16 AND COMPARATIVE EXAMPLES CP 6–CP 7

Production of methyl(R)-2-chloromandelate

The method described above for Examples 11–13 was followed, but carrying out the reaction at a temperature of 50° C. instead of 25° C.

The results obtained are shown in Table VI below.

EXAMPLES 17–21

Production of methyl(R)-2-chloromandelate

The method of Examples 14–16 above was followed, but changing the nature of the solvent and/or the catalyst/substrate molar ratio.

The results obtained are shown in Table VII below.

The results in Tables II–VII show that the best catalysts for producing methyl (R)-2-chloromandelate from methyl (2-chlorophenyl) oxoacetate were the chiral catalysts BINAP Ru (Met)$_2$ and DIOP Ru (Met)$_2$.

These catalysts were advantageously used in a catalyst/substrate molar ratio of 0.5/100 to 4/100. The best solvents were $CH_2Cl_2$ and toluene without the addition of $Et_3N$.

EXAMPLE 22

Application to the Preparation of Tetralol Derivatives, Widely Used in the Pharmaceutical Industry A tetralone was hydrogenated in accordance with the reaction:

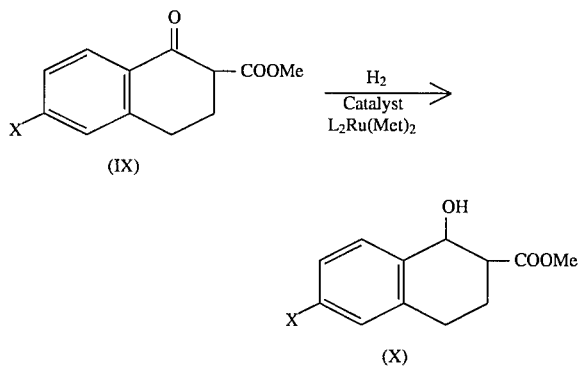

where X was H, MeO, EtO, etc.

$CH_2Cl_2$ was used at a temperature of 80° C. and at a pressure of $10^7$ Pa for 120 hours. Three preparations were carried out, each using 2% of one of the following catalysts, to give quantitative yields:

(a) catalyst [DIOP]Ru(Met)$_2$—100% yield;

(b) catalyst [BINAP]Ru(Met)$_2$—100% yield;

(c) catalyst [CHIRAPHOS]Ru(Met)$_2$—100% yield.

X was MeO in each of the three preparations.

EXAMPLE 23

Preparation of a further intermediate compound of pharmaceutical interest, an ethyl α-chlorohydroxyacetate, from the corresponding ketone in the following reaction:

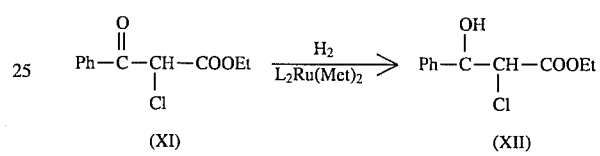

In this reaction, the compound with formula XII was produced from the ethyl α-chloroacetoacetate with formula XI by enantioselective hydrogenation in the presence of 2% of catalyst, in this instance [BINAP]Ru(Met)$_2$, in $CH_2Cl_2$ at 50° C. for a period of 60 hours at $7\times10^6$ Pa; the yield was 100% and the enantiomeric excess e.e was 70% for the anti form and 43% for the syn form (syn/anti ratio: 56/44).

The method of Example 23 is applicable to the preparation of alkyl α-chlorohydroxyacetate compounds (where the alkyl group, e.g. $C_1$–$C_6$, is other than Et).

TABLE I

PREPARATION OF COMPOUND VI

|  | Ex 2 | Ex 3 | Ex 4 | CP 1 |
|---|---|---|---|---|
| Catalyst | BINAP Ru (Met)$_2$ | BINAP Ru (Met)$_2$ | CHIRAPHOS Ru (Met)$_2$ | BINAP Ru (Br)2 |
| catalyst/substrate molar ratio | 0.1/100 | 1/100 | 1/100 | 1/100 |
| temperature | 90° C. | 80° C. | 80° C. | 80° C. |
| pressure of H$_2$ | $10^7$ Pa | $10^7$ Pa | $10^7$ Pa | $10^7$ Pa |
| solvent | MeOH | MeOH | MeOH | MeOH |
| time | 10 h | 10 h | 10 h | 10 h |
| yield | 85% | 95% | 80% | 95% |
| e.e | 79% | 88% | 2% | 60% |

TABLE II

Reaction: methyl 2-(2-chlorophenyl)-2-oxoacetate → methyl (S)-2-(2-chlorophenyl)-2-hydroxyacetate
Conditions: 1% L'Ru(Z)₂, CH₃OH, H₂ 50 atm. 25° C., 24 h.

| Product | Catalyst | Yield % (1) | Enantiomeric excess, % |
|---|---|---|---|
| Ex 5 | BDPP Ru (Met)₂ | 99 | 1 (S) |
| Ex 6 | CHIRAPHOS Ru (Met)₂ | 58 | 21 (S) |
| CP 2 | BDPP RuBr₂ | 71 | 6 (S) |
| CP 3 | CHIRAPHOS RuBr₂ | 47 | 0 |

(1) Determined using ¹H NMR

TABLE III

Conditions: 1% L'Ru(Z)₂, Toluene, H₂ 50 atm. 25° C., 24 h.

| Product | Catalyst | Yield % (1) | Enantiomeric excess, % |
|---|---|---|---|
| Ex 7 | BDPP Ru (Met)₂ | 37 | 29 (S) |
| Ex 8 | DIPAMP Ru (Met)₂ | 21 | 1 (S) |
| CP 4 | DIDAMP Ru Br₂ | 1 | — |

(1) Determined using ¹H NMR

TABLE IV

Conditions: 1% L'Ru(Met)₂, Solvent, H₂, 50 atm, 25° C., 24 h.

| Product | Catalyst | Solvent | Yield % (1) | Enantiomeric excess, % |
|---|---|---|---|---|
| Ex 9 | DIOP Ru (Met)₂ | THF | 17 | 8 (S) |
| Ex 10 | BPPM Ru (Met)₂ | (2) | 34 | 14 (R) |

(1) Determined using ¹H NMR
(2) MeOH + 1% Et₃N

TABLE V

Conditions: 1% L'Ru(Z)₂, CH₂Cl₂, H₂, 50 atm. 25° C., 24 h.

| Product | Catalyst | Yield % (1) | Enantiomeric excess, % |
|---|---|---|---|
| Ex 11 | BDPP Ru (Met)₂ | 99 | 8 (R) |
| Ex 12 | DIOP Ru (Met)₂ | 23 | 41 (S) |
| Ex 13 | DIPAMP Ru (Met)₂ | 41 | 9 (R) |
| CP 5 | DIPAMP Ru Br₂ | 2 | — |

(1) Determined using ¹H NMR

TABLE VI

Conditions: 1% L'Ru(Z)₂, CH₂Cl₂, H₂, 50 atm., 50° C., 24 h.

| Product | Catalyst | Yield % (1) | Enantiomeric excess, % |
|---|---|---|---|
| Ex 14 | DIOP Ru (Met)₂ | 98 | 39 (S) |
| Ex 15 | DIPAMP Ru (Met)₂ | 76 | 14 (R) |
| Ex 16 | BINAP Ru (Met)₂ | 99 | 20 (R) |
| CP 6 | DIOP Ru Br₂ | 88 | 31 (S) |
| CP 7 | DIPAMP Ru Br₂ | 30 | 10 (R) |

(1) Determined using ¹H NMR

TABLE VII

Conditions: 1% L'Ru(Met)₂, Solvent, H₂, 50 atm., 50° C., 24 h.

| Product | Catalyst | Solvent | Yield % (1) | Enantiomeric excess, % |
|---|---|---|---|---|
| Ex 17 | DIPAMP Ru (Met)₂ | MeOH | 67 | 5 (R) |
| Ex 18 | CHIRAPHOS Ru (Met)₂ | CH₂Cl₂ | 92 | 17 (S) |
| Ex 19 | BINAP Ru (Met)₂ (1) | Toluene | 99 | 50 (R) |
| Ex 20 | DIOP Ru (Met)₂ (1) | CH₂Cl₂ | 99 | 49 (S) |
| Ex 21 | DIOP Ru (Met)₂ (1) | CH₂Cl₂ | 99 | 38 (S) |

(1) Catalyst = 4 molar %
(2) Catalyst = 0.5 molar

We claim:

1. A process for enantioselective catalytic hydrogenation of the ketone C=O double bond to a secondary alcohol function, said process using a neutral ruthenium complex as the catalyst and a compound containing a C=O group as the substrate to be hydrogenated, characterised in that it comprises hydrogenation of the carbonyl ketone function of the substrate using $H_2$, in the presence of a diallyl (diphosphino) ruthenium compound with formula

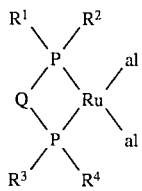  (I)

where al represents an allyl group,

Q represents a hydrocarbon bridge containing at least two catenary carbon atoms and which can contain one to four catenary heteroatoms selected from O, S, N and Si, $R^1$ to $R^4$ may be identical or different and each represents a hydrocarbon group which may be substituted, selected from $C_1$–$C_{18}$ alkyl, $C_5$–$C_7$ cycloalkyl and $C_6$–$C_{12}$ aryl groups.

2. A process according to claim 1 wherein the $R^1R^2P$-Q-$PR^3R^4$ group is selected from the group consisting of chiral ligands BDPP, BINAP, BNPE, BNPPMDS, BPPM, CHIRAPHOS, DIOP, DIPAMP, BPPM, CyDIOP, CyPRONOP, Cy-cy CAPP, CyPOP AE, DEGUPHOS, DPCB, NORPHOS, PNNP, PROPHOS and SKEWPHOS.

3. A process according to claim 1 wherein a solvent is used which is selected from the group consisting of MeOH, EtOH, PrOH, benzene, toluene, xylene, pentane, hexane, heptane, THF, $CH_2Cl_2$, $ClCH_2$—$CH_2Cl$, $Cl_2CH$—$CHCl_2$ and mixtures thereof.

4. A process according to claim 1 wherein the catalyst has formula

 (II)

where

Z is methallyl, and

L is a chiral diphosphino type ligand where the two phosphorus atoms are bonded to each other by a hydrocarbon bridge containing at least two catenary carbon atoms which can contain one to four catenary heteroatoms selected from O, S, N and Si.

5. A process according to claim 4 wherein L* is a BDPP, BINAP, BNPE, BNPPMDS, BPPM, CHIRAPHOS, DIOP or DIPAMP chiral ligand.

6. A process according to claim 1 or claim 4 wherein hydrogenation is carried out under the following conditions:

a temperature of between −20° C. and +150° C., a pressure of $H_2$ between $10^5$ Pa and $1.5 \times 10^7$ Pa, and a catalyst/substrate molar ratio of between 0.01/100 and 10/100.

7. A process according to claim 1 or claim 4 wherein hydrogenation is carried out under the following conditions:

a temperature of 15° C. to 100° C., a pressure of $H_2$ between $5 \times 10^5$ Pa and $10^7$ Pa, a catalyst/substrate molar ratio of between 0.5/100 and 4/100, and a substrate concentration of between 0.4 mole/liter and 0.8 mole/liter.

8. A process according to claim 4 wherein hydrogenation is carried out in a solvent selected from $CH_2Cl_2$ and toluene in the presence of a catalyst with formula II where L* is DIOP or BINAP under the following conditions:

a temperature of 25° C. to 50° C., a pressure of $H_2$ between $5 \times 10^6$ Pa and $10^7$ Pa, a catalyst/substrate molar ratio in the order of 1/100, and a substrate concentration of between 0.4 mole/liter and 0.8 mole/liter.

9. A process according to any one of claims 1 to 8 characterised in that the substrate containing the ketone C=O double bond is selected from alpha- and betaketoesters.

10. Use of a process according to any one of claims 1 to 8 to obtain an enantiomerically pure isomer selected from the group constituted by (R)-pantolactones, ethyl (R)-4-chloro-3-hydroxybutanoates, and methyl (R)-2-chloromandelates.

11. A process according to any one of claims 1 to 9 applied to the preparation of a tetralol derivative.

12. A process according to any one of claims 1 to 9 applied to the preparation of an alkyl α-chlorohydroxyacetate.

13. A process according to claim 1 wherein al is $CH_2CH=CH_2$ or $CH_2C(CH_3)=CH_2$.

14. A process according to claim 4, wherein hydrogenation is carried out under the following conditions:

a temperature of between −20° C. and +150° C., a pressure of $H_2$ between $10^5$ Pa and $1.5 \times 10^7$ Pa, and a catalyst/substrate molar ratio of between 0.01/100 and 10/100.

15. A process according to claim 4, wherein hydrogenation is carried out under the following conditions:

a temperature of between −15° C. to 100° C., a pressure of $H_2$ between $5 \times 10^5$ Pa and $10^7$ Pa, a catalyst/substrate molar ratio of between 0.5/100 and 4/100, and a substrate concentration of between 0.4 mole/liter and 0.8 mole/liter.

* * * * *